[19] United States Patent
Reuter et al.

[11] 4,324,694
[45] Apr. 13, 1982

[54] SUPPORTED CATALYSTS CONTAINING VANADIUM PENTOXIDE, TITANIUM DIOXIDE, PHOSPHORUS, RUBIDIUM AND/OR CESIUM, WITH OR WITHOUT ZIRCONIUM DIOXIDE

[75] Inventors: Peter Reuter, Bad Duerkheim; Kurt Blechschmitt, Schifferstadt; Friedrich Wirth, Ludwigshafen, all of Fed. Rep. of Germany

[73] Assignee: BASF Aktiengesellschaft, Ludwigshafen, Fed. Rep. of Germany

[21] Appl. No.: 157,782

[22] Filed: Jun. 9, 1980

[30] Foreign Application Priority Data

Jun. 26, 1979 [DE] Fed. Rep. of Germany ....... 2925682

[51] Int. Cl.³ .................. B01J 21/06; B01J 23/04; B01J 23/22; B01J 27/16
[52] U.S. Cl. .................. 252/435; 252/437; 260/346.4
[58] Field of Search .............. 252/435, 437; 260/346.4

[56] References Cited

U.S. PATENT DOCUMENTS 3,894,971  7/1975  Reuter et al. .................. 252/437
4,007,136  2/1977  Blechschmitt et al. ............ 252/476
4,077,984  3/1978  Blechschmitt et al. ........ 252/435 X

FOREIGN PATENT DOCUMENTS 1496832  1/1978  United Kingdom .

Primary Examiner—W. J. Shine
Attorney, Agent, or Firm—John H. Shurtleff

[57] ABSTRACT

A supported catalyst, containing vanadium pentoxide, titanium dioxide, phosphorus, rubidium and any optionally added cesium, with or without zirconium dioxide, in which the catalytic material contains from 1 to 40% by weight of $V_2O_5$, from 60 to 99% by weight of $TiO_2$ and/or $ZrO_2$ and, based on the total amount of $TiO_2$, $ZrO_2$ and $V_2O_5$, up to 2% by weight of phosphorus and up to 1.5% by weight of rubidium and/or cesium, and which comprises two layers, of which the inner layer contains more than 0.2 and up to 2% by weight of phosphorus, but no rubidium and/or cesium, and the outer layer contains from 0 to 0.2% by weight of phosphorus and from 0.02 to 1.5% by weight of rubidium and/or cesium, the outer layer accounting for from 10 to 90% by weight of the total catalytic material.

12 Claims, No Drawings

SUPPORTED CATALYSTS CONTAINING VANADIUM PENTOXIDE, TITANIUM DIOXIDE, PHOSPHORUS, RUBIDIUM AND/OR CESIUM, WITH OR WITHOUT ZIRCONIUM DIOXIDE

The present invention relates to a novel supported catalyst containing vanadium pentoxide, titanium dioxide, phosphorus, rubidium and/or cesium, with or without zirconium dioxide, and to its use for the preparation of phthalic anhydride by catalytic gas phase oxidation of o-xylene or naphthalene.

Catalysts containing titanium dioxide and vanadium pentoxide have been disclosed as oxidation catalysts for the preparation of carboxylic acids or carboxylic anhydrides from aromatic or unsaturated aliphatic hydrocarbons. Amongst these catalysts, it is the supported catalysts described, for example, in French Pat. No. 1,480,078, in which an inert carrier is coated with a catalytic material, which have become important for the industrial continuous preparation of phthalic anhydride (PA) from o-xylene or naphthalene.

In order to improve the life of such catalysts, Belgian Pat. No. 737,587 proposes adding phosphorus compounds to the catalytic material. It is only after a few months that the phosphorus-containing catalysts thus obtained can be exposed to the maximum hydrocarbon loading of up to 40 g/m$^3$ (S.T.P.) of air. In order to overcome this disadvantage, German Published Application DAS 2,212,964 has proposed phosphorus-containing catalysts which contain only up to 0.3% by weight of phosphorus, if any, in the outer layer of the catalytic material, and from 0.3 to 6% by weight of phosphorus in the catalytic material below this outer layer. Catalysts of this type can be exposed, shortly after startup, to the full loading of 40 g of o-xylene or naphthalene per m$^3$ (S.T.P.) of air, without damaging the catalyst.

These phosphorus-containing catalysts have proved useful in industrial operation. They have the additional advantage, over phosphorus-free catalysts, that they can be used without the conventional addition of sulfur dioxide to the mixture of o-xylene or naphthalene and air and hence serve to reduce pollution of the environment. However, they have the disadvantage that the maximum loading which can be used is 40 g of o-xylene or naphthalene per m$^3$ (S.T.P.) of air. If more o-xylene, for example up to 46 g per m$^3$ (S.T.P.) of air, is used, hot spots form in a narrow zone within the catalyst bed, and attain temperatures exceeding 500° C. At such high temperatures, the catalyst suffers damage and the catalyst life is accordingly substantially shortened; furthermore, the yield is reduced.

German Laid-Open Applications DOS Nos. 2,421,406 and DOS 2,436,009 describe catalysts which contain titanium dioxide and vanadium pentoxide and in which the catalytic material contains from 0.01 to 1.5% by weight of rubidium and/or cesium. These catalysts allow the loading of o-xylene or naphthalene per m$^3$ (S.T.P.) of air to be increased to 50–150 g whilst retaining a high yield and long life. However, the advantageous properties of the phosphorus-containing catalysts in respect of long life cannot be achieved with these catalysts. It is a further disadvantage that they can only be operated for at most a few months without addition of sulfur dioxide to the mixture of o-xylene and air, and even then only with an o-xylene loading of less than 50 g per m$^3$ (S.T.P.) of air. After a few months' operation, the quality of the PA obtained deteriorates and this makes it necessary rapidly to raise the salt bath temperature, which in turn inescapably reduces the yield. In order to be able to continue to use the catalyst economically, it becomes unavoidable to add sulfur dioxide to the synthesis mixture.

The requisite amount of sulfur dioxide is from about 0.2 to 1.5% by weight, based on the amount of o-xylene. It pollutes the environment and is a not insignificant cost factor.

The quality of the PA obtained is assessed in terms of the content of phthalide, an insufficiently oxidized by-product, in the PA, since phthalide presents particular difficulties in the purification of PA.

On the one hand, the severe pollution of the environment by the sulfur dioxide passing into the atmosphere makes it desirable to use the catalysts without adding SO$_2$ to the gas mixture, whilst on the other hand it is desirable to attain very high loadings of o-xylene or naphthalene per m$^3$ (S.T.P.) of air, since then a smaller amount of air has to be compressed, which leads to substantial savings in electricity costs or steam costs, as a result of which the economics of the process can be greatly improved.

The two measures, namely SO$_2$-free operation, and operation with high o-xylene loadings of air, are mutually exclusive in the case of the conventional catalysts. It is an object of the present invention to provide a catalyst which can be used both without addition of SO$_2$ and with high o-xylene loadings of the air, and which gives the requisite advantageous results in respect of PA yield and purity.

The obvious approach of using catalysts which contain both phosphorus and rubidium and/or cesium in the catalytic material did not achieve the desired object. It is true that high o-xylene loadings of the air, namely greater than 40 g per m$^3$ (S.T.P.), are achieved with these catalysts, but they give a lower yield than if only the phosphorus-containing catalysts or only the catalysts containing rubidium and/or cesium are used. Furthermore, catalysts containing rubidium and cesium can only be used for a few months without addition of SO$_2$ to the synthesis mixture.

We have found that the object of the invention is achieved and that a supported catalyst which contains vanadium pentoxide, titanium dioxide, phosphorus, rubidium and/or cesium, with or without zirconium dioxide, and which has been produced by applying an appropriate solution or suspension of the components to an inert carrier, application being effected in two layers in such a way that the catalyst, after drying, carries an 0.02–2 mm thick coating of the catalytic material, possesses the desired advantages, if the catalytic material used contains from 1 to 40% by weight of V$_2$O$_5$, from 60 to 99% by weight of TiO$_2$ and any optionally added ZrO$_2$ and, based on the total amount of TiO$_2$, ZrO$_2$ and V$_2$O$_5$, up to 2% by weight of phosphorus and up to 1.5% by weight of rubidium and/or cesium, and if the application of the material is effected by first providing the preheated carrier with a layer of the catalytic material which contains more than 0.2 and up to 2% by weight of phosphorus but no rubidium and/or cesium and then providing the carrier, thus coated with a first, inner layer, with a second, outer layer of the catalytic material which contains from 0 to 0.2% by weight of phosphorus and from 0.02 to 1.5% by weight of rubidium and/or cesium, the coating being applied in such a way that the catalytic material of the outer layer— which is free from phosphorus or has the lower phosphorus content—of the supported catalyst accounts for from 10 to 90% by weight of the total catalytic material.

In addition to the constituents mentioned, the catalytic material may contain small amounts, for example up to 10% by weight, of an oxide of the metals niobium, tin, silicon, antimony, hafnium, molybdenum or tungsten.

$TiO_2$ is advantageously present in the novel catalysts as anatase having an inner surface area of from 5 to 30, especially from 5 to 20, $m^2/g$. The inner surface area of the zirconium dioxide should preferably be from 2 to 25, especially from 2 to 20, $m^2/g$. These oxides are employed in a finely divided form.

It is an essential feature of the invention that the outer layer of the catalytic material of the novel catalysts contains no phosphorus, or only up to 0.2% by weight of phosphorus, and from 0.02 to 1.5% by weight, preferably from 0.05 to 0.5% by weight, of rubidium and/or cesium, whilst the catalytic material below it is free from rubidium and cesium and contains from 0.2 to 2% by weight, preferably from 0.3 to 1.2% by weight, of phosphorus, all the above percentages being based on the total amount of $V_2O_5$ and $TiO_2$, plus $ZrO_2$, if the last-mentioned is present.

The outer layer of the supported catalyst preferably accounts for at most half the total catalytic material.

The catalysts of the present invention are supported catalysts which consist of an inert carrier and a thin layer of catalytic material applied thereto. The inert carrier is a material of very low porosity which preferably has an inner surface area of from 0 to 3 $m^2/g$ such as quartz, porcelain, fused alumina, silicon carbide or fused or sintered silicates. The carriers are advantageously in the form of granules, pills, beads or other moldings, but ring-shaped carriers are particularly preferred.

The total active material on the carrier advantageously accounts for from 2 to 140, preferably from 2 to 50, % by weight, based on the carrier.

The vanadium pentoxide content of the supported catalysts is preferably from 0.05 to 3% by weight.

The coating of the carrier with the catalytic material is advantageously effected by working a solution or suspension of a vanadium compound and of a phosphorus compound, with or without a rubidium compound or cesium compound, into a paste with finely divided anatase, with or without zirconium dioxide, and spraying the paste onto the carrier, which has been preheated to 200°–450° C., in a coating kettle. It may be advantageous subsequently to heat the catalyst at 400°–500° C. Examples of suitable vanadium compounds are vanadyl oxalate, vanadyl formate, vanadyl tartrate, ammonium vanadate and vanadium pentoxide, whilst examples of suitable phosphorus compounds are alkali metal phosphates and ammonium phosphates, the corresponding metaphosphates and pyrophosphates and alkaline earth metal phosphates, phosphoric acid and esters of phosphoric acid. Examples of suitable rubidium compounds and cesium compounds are the oxides and other oxygen-containing compounds which at elevated temperatures are converted to the oxides, eg. carbonates, acetates and nitrates. The individual layers are produced by separate application of the corresponding catalytic materials, in the desired sequence.

The novel catalysts may be used, for example, for the preparation of phthalic anhydride by oxidizing o-xylene or naphthalene, for the preparation of maleic anhydride by oxidizing benzene or unsaturated aliphatic $C_4$-hydrocarbons, for the preparation of pyromellitic anhydride by oxidizing durene or other 1,2,4,5-tetraalkylbenzenes, for the preparation of naphthalic acid from acenaphthene and for the preparation of quinones by oxidizing naphthalene to naphthoquinone or by oxidizing anthracene, substituted indans or diphenylmethane compounds, eg. 2-methyldiphenylmethane, to anthraquinone by means of air or an oxygen-containing gas.

The use of the novel catalyst for the preparation of phthalic anhydride by oxidizing o-xylene or naphthalene with air is of particular industrial interest. The catalyst can be put into operation in a conventional manner, for example as described in French Pat. No. 1,480,078.

The novel catalyst can also advantageously be employed in such a way that it only occupies the first 25–70% by volume (in the direction of flow of the mixture of hydrocarbon and oxygen-containing carrier gas) in the reaction tube. If this method is used, the remaining 30–75 percent by volume of the tube are filled with a conventional catalyst, for example with a catalyst as described in German Published Application DAS 1,769,998, consisting, for example, of an inert carrier and a catalytic material which contains from 66 to 99% by weight of titanium dioxide and from 1 to 40% by weight of vanadium pentoxide together with from 0.02 to 0.8% by weight, based on titanium dioxide, of phosphorus in the form of a phosphorus compound.

EXAMPLE 1

(a) Preparation of the catalyst 1,200 g of steatite rings having an external diameter of 8 mm and a length of 6 mm are heated at 260° C. in a coating kettle and are sprayed therein with an aqueous suspension, consisting of 250 g of anatase having an inner surface area of 11 $m^2/g$, 81 g of formamide, 500 g of water, 35.9 g of vanadyl oxalate (corresponding to 16 g of $V_2O_5$) and 4.44 g of ammonium dihydrogen phosphate (corresponding to 3.66 g of $PO_4^{3-}$), until the active material accounts for 5% by weight of the supported catalyst. The coating of active material contains 94% by weight of $TiO_2$ and 6% by weight of $V_2O_5$ and 0.45% by weight, based on the total amount of anatase and vanadium pentoxide, of phosphorus as phosphate.

Thereafter, an aqueous suspension consisting of 250 g of anatase having an inner surface area of 11 $m^2/g$, 81 g of formamide, 500 g of water, 35.9 g of vanadyl oxalate (corresponding to 16 g of $V_2O_5$) and 0.54 g of rubidium carbonate is sprayed onto the catalyst until the total content of active material in the supported catalyst is 10% by weight. The second coating contains 94% by weight of $TiO_2$, 6% by weight of $V_2O_5$ and 0.15% by weight of rubidium, based on the total amount of anatase and vanadium pentoxide.

(b) Oxidation 1,180 g of the catalyst are introduced into a 3.25 m long iron tube having an internal diameter of 25 mm. The iron tube is surrounded by a salt melt to regulate its temperature. Per hour, 4.5 $m^3$ (S.T.P.) of air, charged with up to about 60 g of 97 percent strength by weight o-xylene per $m^3$ of air are passed downward through the tube. This gives the results summarized in the Table below (the yield being the phthalic anhydride obtained, in percent by weight, based on 100% pure o-xylene).

| Duration of experiment, months | Xylene loading of the air, g of o—xylene/m³ (S.T.P.) | Salt bath temperature (°C.) | Yield % by weight | Phthalide content in the crude PA (%) |
| --- | --- | --- | --- | --- |
|  | 36.0 | 380 | 112.1 | traces |
| 0.5 | 50.3 | 372 | 113.6 | traces |
| 1.0 | 60.8 | 364 | 113.6 | 0.001 |
| 9.0 | 62.3 | 364 | 114.1 | 0.002 |

After the experiment has been run for 9 months, no drop in catalyst activity is detectable, as shown by the virtually unchanged content of phthalide in the phthalic anhydride obtained. Addition of sulfur dioxide to the synthesis gas is not necessary.

EXAMPLE 2

(a) Preparation of catalyst I

The catalyst is prepared as described in Example 1.

(b) Preparation of catalyst II 600 g of steatite rings having an external diameter of 8 mm and a length of 6 mm are heated at 260° C. in a coating kettle and are sprayed therein with a suspension consisting of 200 g of anatase, having an inner surface area of 11 m²/g, 36.6 g of vanadyl oxalate (vanadium content corresponding to 41% of $V_2O_5$), 200 g of water, 50 g of formamide and 2.44 g of ammonium hydrogen phosphate until the weight of the catalytic material applied is 10% of the total weight of the catalyst. The catalyst layer thus applied consists of 0.3% by weight of phosphorus, 7.0% by weight of vanadium pentoxide and 92.7% by weight of titanium dioxide.

(c) Oxidation 680 g of catalyst II, followed by 500 g of catalyst I, are introduced into a 3.25 m long iron tube having an internal diameter of 25 mm. The experiments are carried out as described in Example 1 and give the following results:

| Duration of experiment, months | Xylene loading of the air, g of o—xylene/m³ (S.T.P.) | Salt bath temperature (°C.) | Yield % by weight | Phthalide content in the crude PA (%) |
| --- | --- | --- | --- | --- |
|  | 35 | 379 | 111.8 | traces |
| 0.5 | 49 | 372 | 113.2 | traces |
| 1.0 | 62.1 | 362 | 113.2 | traces |
| 10.0 | 61.8 | 360 | 113.9 | traces |

After the experiment has run for 10 months, the catalyst can still be used without addition of sulfur dioxide to the synthesis gas. The phthalide content in the phthalic anhydride obtained is unchanged.

We claim:

1. A supported catalyst which contains vanadium pentoxide, titanium dioxide, phosphorus, rubidium and/or cesium, with or without zirconium dioxide, obtained by applying an appropriate solution or suspension of the components in two layers onto a preheated inert carrier, so that after drying, the catalyst carries an 0.02-2 mm thick coating of the catalytic material, wherein the catalytic material used contains from 1 to 40% by weight of $V_2O_5$, from 60 to 99% by weight of $TiO_2$ and any optionally added $ZrO_2$ and, based on the total amount of $TiO_2$, $ZrO_2$ and $V_2O_5$, up to 2% by weight of phosphorus and up to 1.5% by weight of rubidium and/or cesium, and the application of the material is effected by first providing the preheated carrier with a layer of the catalytic material which contains more than 0.2 and up to 2% by weight of phosphorus but no rubidium and/or cesium and then providing the carrier, thus coated with a first, inner layer, with a second, outer layer of the catalytic material which contains from 0 to 0.2% by weight of phosphorus and from 0.02 to 1.5% by weight of rubidium and/or cesium, the coating being applied in such a way that the catalytic material of the outer layer—which is free from phosphorus or has the lower phosphorus content—of the supported catalyst accounts for from 10 to 90% by weight of the total catalytic material.

2. A catalyst as claimed in claim 1 wherein the inert carrier has an inner surface area of from 0 to 3 m²/g.

3. A catalyst as claimed in claim 2 wherein said inert carrier is selected from the group consisting of quartz, porcelain, fused alumina, silicon carbide and fused or sintered silicates.

4. A catalyst as claimed in claim 2 wherein the inert carrier is in the form of a ring shaped carrier.

5. A catalyst as claimed in claim 1 wherein said outer catalyst layer contains 0.05 to 0.5% by weight of said rubidium and/or cesium, based upon the total amount of $TiO_2$, $ZrO_2$ and $V_2O_5$.

6. A catalyst as claimed in claim 1 wherein said inner catalyst layer contains from 0.3 to 1.2% by weight of phosphorous, based upon the total amount of $TiO_2$, $ZrO_2$ and $V_2O_5$.

7. A catalyst as claimed in claim 1 wherein the outer catalyst layer contains no phosphorous.

8. A catalyst as claimed in claim 1 wherein the outer catalyst layer accounts for, at most, half the total catalytic material.

9. A catalyst as claimed in claim 1 wherein the $TiO_2$ is a finely divided anatase having an inner surface area of about 5 to 30 m²/g, and the $ZrO_2$ is a finely divided oxide having an inner surface area of about 2 to 25 m²/g.

10. A catalyst as claimed in claim 1 wherein the $V_2O_5$ content of the catalytic material in each layer is about 0.05 to 3% by weight.

11. A catalyst as claimed in claim 1 wherein the total active catalytic material on the carrier is from about 2 to 140% by weight based on the carrier.

12. A catalyst as claimed in claim 1 wherein the total active catalytic material on the carrier is from about 2 to 50% by weight based on the carrier.

* * * * *